(12) United States Patent
Ulene et al.

(10) Patent No.: US 11,903,534 B2
(45) Date of Patent: Feb. 20, 2024

(54) PORTABLE URINAL

(71) Applicant: MyLooCo, Sherman Oaks, CA (US)

(72) Inventors: Valerie Ulene, Los Angeles, CA (US);
Byrdie Pompan, Los Angeles, CA (US)

( * ) Notice: Subject to any disclaimer, the term of this patent is extended or adjusted under 35 U.S.C. 154(b) by 0 days.

(21) Appl. No.: 17/875,746

(22) Filed: Jul. 28, 2022

(65) Prior Publication Data

US 2023/0035907 A1 Feb. 2, 2023

Related U.S. Application Data

(60) Provisional application No. 63/227,270, filed on Jul. 29, 2021.

(51) Int. Cl.
*A47K 11/12* (2006.01)

(52) U.S. Cl.
CPC .................................. *A47K 11/12* (2013.01)

(58) Field of Classification Search
CPC ....................................................... A47K 11/12
USPC .............. 4/144.1, 301, 449, 144.2; 600/573; 604/327
See application file for complete search history.

(56) References Cited

U.S. PATENT DOCUMENTS

| 4,667,881 A | 5/1987 | Michelotti | |
|---|---|---|---|
| 5,884,802 A * | 3/1999 | Leibowitz | B65D 25/2882 222/465.1 |
| 5,894,608 A * | 4/1999 | Birbara | A61F 5/4556 604/319 |
| 5,953,763 A | 9/1999 | Gouget | |
| 6,578,206 B1 * | 6/2003 | LaBrash | A47K 11/12 4/144.1 |
| 7,251,843 B2 * | 8/2007 | Malloy | A47K 11/12 4/144.1 |
| 2004/0154937 A1 | 8/2004 | Cho | |
| 2014/0082833 A1 * | 3/2014 | Guo | A47K 11/12 4/144.4 |
| 2017/0325641 A1 * | 11/2017 | Rudolph | A61F 5/4556 |

FOREIGN PATENT DOCUMENTS

| CN | 204121341 | | 1/2015 | |
|---|---|---|---|---|
| CN | 204293412 | | 4/2015 | |
| CN | 210249891 | | 4/2020 | |
| GB | 2282761 | A * | 4/1995 | ............ A61G 9/006 |
| JP | 2001269288 | A * | 10/2001 | |
| JP | 2005052608 | A * | 3/2005 | |

OTHER PUBLICATIONS

International Search Report and Written Opinion, issued on PCT Patent Application No. PCT/US2022/038786, dated Oct. 17, 2022.

* cited by examiner

*Primary Examiner* — Lori L Baker
(74) *Attorney, Agent, or Firm* — McCarter & English, LLP; James M. Smedley; Alex Korona (57) ABSTRACT

A portable urinal in the form of a vessel with a reservoir, lid, funnel, one or more handles, and internal fluid diverting features in various arrangements and combinations. The components of the portable urinal are useful for mitigating odor and directing fluid to dampen sound. The funnel of the portable urinal can be aligned to direct fluid toward the internal diverting features to dampen the sound of fluid flowing into the reservoir.

19 Claims, 3 Drawing Sheets

PORTABLE URINAL

CROSS-REFERENCE TO RELATED APPLICATIONS

This application claims the benefit of U.S. Provisional Application No. 63/227,270, filed Jul. 29, 2021 and entitled PORTABLE URINAL, the entire disclosure of which is hereby incorporated by reference in its entirety.

FIELD OF THE INVENTION

The present invention generally relates to portable urinals, and more particularly, to an ergonomic portable urinal provided with improved features including, for example, fluid directive, odor mitigating, and sound-dampening features.

BACKGROUND

In general, urinals in the prior art have been developed for use by individuals, for example, medically infirm individuals who are physically incapable of walking to a bathroom. Many such portable urinals are configured with open-mouthed, plastic vessels that may be placed between the legs of an individual when the individual is in a supine, seated or erect position. Though some such urinals may include caps or lids, most do not. Therefore, such urinals are not effective in trapping or otherwise mitigating odors, and are substantially prone to spills. Moreover, most urinals are formed using opaque or semi-opaque plastic material, generally, for the purpose of distorting the contents of the urinal, however, such materials are inherently noisy when such urinals are in use, for example, when an individual urinates into the vessel, the urinary stream may directly hit a bottom of the vessel. Furthermore, urinals in the prior art lack sufficient ergonomic or otherwise attractive design features.

Therefore, there is a need in the art for an ergonomic and functional portable urinal that provides enhanced sound-dampening means, odor-trapping functionalities, and easy clean-up solutions, amongst other improved features. These and other features and advantages of the present invention will be explained and will become obvious to one skilled in the art through the summary of the invention that follows.

BRIEF DESCRIPTION OF THE DRAWINGS

Accompanying this written specification is a collection of drawings of exemplary embodiments of the present disclosure. One of ordinary skill in the art would appreciate that these are merely exemplary embodiments, and additional and alternative embodiments may exist and still within the spirit of the disclosure as described herein.

OBJECTS AND BRIEF SUMMARY OF THE INVENTION

It is an objective of the present invention to provide an improved portable urinal.

It is another objective of the present invention to provide an ergonomic portable urinal.

It is another objective of the present invention to provide a portable urinal having sound-dampening features. In some examples, a funnel component may be provided to support sound-dampening functions. In some scenarios, the funnel component may be formed of a one or more layers of a thick-walled material, for example, a plastic or silicone material, configured to decrease the sound emitted from the urinal during its use. In some embodiments, the funnel component may optionally include a one or more additional layers formed of a sound-dampening material, for example, double-shot silicone.

It is another objective of the present invention to provide a generally central opening through a body of a portable urinal, to provide, among other things, at least one handle for ease of use of the portable urinal.

It is another objective of the present invention to provide a funnel component configured to channel or otherwise direct a stream of fluid towards a deflection wall to dampen sounds of liquids entering the urinal.

It is another objective of the present invention to provide a portable urinal configured to prevent odors from escaping the interior of the portable urinal, for example, by providing a funnel component and/or a cover configured substantially cover the portable urinal to retain odors and substantially prevent the odors from escaping the portable urinal. In some scenarios, a funnel component may mitigate odor as the funnel may be designed to prevent the urinal from having an otherwise wide-open mouth or opening.

It is another objective of the present invention to provide a portable urinal providing a means to decrease the risk of spills, for example, by providing a funnel component and/or a cover which may be configured to decrease the likelihood that contents of the portable urinal will spill if the urinal falls over.

It is another objective of the present invention to provide a portable urinal configured to be easily cleanable, for example, by providing a portable urinal with a removable funnel component which may be easily separated from a body of the urinal to enable cleaning of the individual components.

It is another objective of the present invention to provide a portable urinal having a funnel component configured to capture a stream of urine from a wide opening, and direct the stream towards a small opening at a bottom section of the funnel component. In some examples, the stream may be directed to form a controlled cascade through, for example, an inner handle lining disposed on a deflection portion of the urinal body.

It is another objective of the present invention to provide a portable urinal having one or more adhesive absorbent pads configured to assist in drying.

It is another objective of the present invention to provide a portable urinal having a lighting module. In some examples, the urinal device lighting module may be configured to provide light during nighttime usage. In some scenarios, the urinal device lighting module may be configured to assist users in quickly locating the urinal device. In some embodiments, the urinal device lighting module may be disposed on a bottom side of the urinal device. The weight of the urinal device lighting module may anchor the urinal device, for example, the lighting module may prevent the portable urinal from tipping over to prevent spills.

It is another objective of the present invention to provide a holder for docking or holding the portable urinal. In some embodiments, the holder may be configured as an accessory for the urinal device and may include a lighting module. In some examples, the holder lighting module may be configured to emit light when the urinal device is placed on it. In some examples, the holder lighting module may be configured to provide light during nighttime usage. In some scenarios, the urinal device lighting module may be configured to assist users in quickly locating the urinal device. In some examples, the holder may support an upright position of the urinal device.

In accordance with embodiments of the present invention, a liquid retaining apparatus in accordance with the present disclosure may be configured as a portable urinal and may comprise a vessel having two fluid paths, each path originating at a top end of the vessel being an opening and meeting at a bottom end of the vessel being a reservoir portion, wherein the vessel may further include a middle section comprising a fluid deflection wall, and the liquid retaining apparatus may further comprise a funnel component having a top section adapted to engage with the top opening of the vessel. In some embodiments, the two fluid paths of the vessel may be in fluid communication with one another. In some embodiments, a void may be formed through the middle section of the vessel, such that the middle section may define one or more handles of the vessel. In some embodiments, the funnel component top section may comprise a border element disposed around an edge portion of the top section, the border element having a bottom side comprising a slot corresponding to an edge portion of the opening at the top end of the vessel to support secured engagement of the funnel component with the vessel. In some examples, the funnel component may be configured to direct liquid towards the deflection wall formed at the middle section of the vessel to dampen sound created by fluids entering the vessel. In some scenarios, a cover may be configured to engage with the top end of the vessel and cover the top opening of the vessel and the funnel component.

In accordance with embodiments of the present invention, a liquid retaining apparatus in accordance with the present disclosure may be configured as a portable urinal and may comprise a vessel comprising a tubular structure forming a loop having a flat bottom section being a reservoir portion and a top section having an opening, wherein the loop may comprise a middle section formed with at least one interior sidewall comprising a top portion with a fluid deflection portion, and a funnel component which may have a top opening extending towards a bottom opening and having interior side walls which taper down from the top opening to the bottom opening to form a conical channel. In some embodiments, a lip portion of the funnel component may be disposed around a border of the top opening of the funnel component and may be configured to support connection of the funnel component to an edge portion of the top section of the vessel. In some embodiments, a bottom side of the lip portion may be formed with a slot configured to receive the top section of the vessel. In some embodiments, the funnel component may be configured to direct liquid towards the deflection portion of the middle section to deflect liquid entering the vessel and limit sound created by fluid entering the vessel. In some embodiments, a void may be formed in the middle section of the vessel to form a pair of handles enabling the vessel to be easily grasped by a user by gripping at least one of the handles of the pair. In some embodiments, instead, or in addition to the void, a compression section may be formed in the middle section of the vessel, at a joint or compression point connecting two opposing side walls of the vessel to form a pair of handles enabling the vessel to be easily grasped by a user by gripping at least one of the handles of the pair.

In accordance with embodiments of the present invention, a liquid retaining apparatus in accordance with the present disclosure may be configured as a portable urinal and may comprise a vessel which may have a top section with an opening formed with an edge portion, a bottom section being a reservoir portion, and two channels beginning at the opening of the top portion, diverging at a middle section and meeting at the reservoir portion of the vessel, the two channels being in fluid communication with one another and each channel comprising an interior side wall meeting at a middle section of the vessel and forming a deflection portion, and a funnel member formed as a conical structure tapering from a wide upper end to a narrow lower end and comprising a border element disposed around the wide upper end, the border element having a bottom side formed with a slot adapted to receive the edge portion of the vessel, wherein the funnel member is configured to direct liquid towards the deflection portion of the vessel to dampen sound created by fluids entering the vessel. In some embodiments, the funnel member may be formed of a silicon material and the wide upper end of the funnel member may be configured to fit female genitalia to form at least a partial seal, for example, to support use of the vessel as a portable urinal by female users. In some embodiments, the deflection portion may be configured as a baffle to interrupt liquid flow. In some embodiments, the funnel component and deflection portion of the vessel may collectively prevent liquid entering the vessel from making direct contact with the reservoir portion of the vessel. In some embodiments, the edge portion of the vessel may be formed with a depression extending around a perimeter of the top portion, the depression corresponding to and adapted to engage with the slot formed in the border element of the funnel member. In some embodiments, the middle section may define a void or a compression section which forms a pair of handles configured to enable the vessel to be easily grasped by a user by gripping at least one of the handles.

DETAILED DESCRIPTION OF ILLUSTRATIVE EMBODIMENTS

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

Embodiments of the present invention are directed towards a portable urinal comprising a vessel which may be formed as urinal body member, a funnel component, and a cover. Some embodiments may comprise additional or fewer components without departing from the spirit and scope of the disclosed device.

In accordance with embodiments of the present invention, a urinal body may be formed with two fluid paths, for example, tubular channels, connected at their top and bottom ends. The two fluid paths may be in fluid communication with one another. The connection of the two tubular channels to one another at their respective top and bottom ends may define a hollow recess in a general center of the urinal body member to form a pair of handles and enable the urinal body to be easily grasped by a user by gripping at least one of the tubular channels. In some examples, the urinal body may include a compression section configured as a joint connecting a first side wall to a second side wall of the urinal body to similarly form a pair of handles. In some examples, one such handle may include a grip portion, to further facilitate easy grasping of the urinal body member.

In accordance with embodiments of the present invention, a removable cover may be provided to cover an opening formed at a top section of the urinal body and, optionally, a top end of the funnel component. In some examples, the cover may friction fit with the protruding opening configured in the urinal body, for example, by substantially corresponding to the outer configuration of the protruding opening of the urinal body. In some embodiments, the removable cover may be a screw-type cover which may cooperate with corresponding screw formations molded in the opening formed at the top section of the urinal body. The cover may be configured to seal the urinal and prevent spilling of the urinal contents.

In accordance with embodiments of the present invention, a funnel component may be provided to connect to a top portion of the urinal body. The funnel component may be configured in a generally conical shape to direct fluids in a desired direction. In any embodiment, the funnel component may be formed in any similarly suitable shape configured to similarly channel fluids.

In some scenarios, equivalent continuous sound pressure level (LAeq) of liquids increases logarithmically with increased flow rate for many types of small to medium sized water features. Additionally, an increase in height (e.g. distance) of falling liquid significantly increases the LAeq. Therefore, a reduction in liquid flow rate and a reduction in distance falling liquid will need to travel may significantly reduce the sound emitted from the collision of the liquid with a liquid container, for example, a urinal. In accordance with embodiments of the present invention, the urinal device disclosed herein may be configured with a funnel which may both reduce the flow rate of fluids introduced to the funnel and may decrease the distance the liquid must travel to enter the urinal body to reduce the sound levels that would otherwise be created by the introduction of the liquid into the urinal container and support the sound-dampening features of the urinal.

Turning now to FIGS. 1-10, generally shown is a portable urinal device in accordance with an embodiment of the present invention. As shown in the drawings, a portable urinal device 100 may comprise a body member 110, a funnel component 120, and a cover 130.

FIGS. 1-4 depict demonstrative views of an exemplary portable urinal device in accordance with embodiments of the present invention. As shown in FIGS. 1-4, a vessel or portable urinal 100 may comprise a body member 110 formed with two tubular channels 111 and 112, respectively, connected at their top and bottom ends 113 and 114, respectively. In some examples, the top end 113 of the body member 100 may be formed with an opening 117, and the bottom end 114 may define a liquid reservoir portion. The connection of the two tubular channels 111 and 112 to one another at their respective top and bottom ends 113 and 114 may define a hollow recess 115 in a general center of the body member 110 to enable the body member 110 to be easily grasped by a user by gripping an exterior portion of at least one of the tubular channels 111 and 112. In some examples, the hollow recess 115 formed in the body member 110 may define handles, corresponding to the two tubular channels 111 and 112. In some examples, one such handle may include a grip portion, to further facilitate easy grasping of the body member 110. In some scenarios, the hollow recess 115 formed in the body member 110 may create an internal apex 116 in the urinal body. A deflection portion or wall 118 may be disposed or formed on a middle section of the body member 110, for example, on or near the internal apex 116. The top end 113 of the body member 110 may also include an opening 117 adapted to engage with a funnel component 120, and may be covered by a cover 130.

Figures 1, 2:
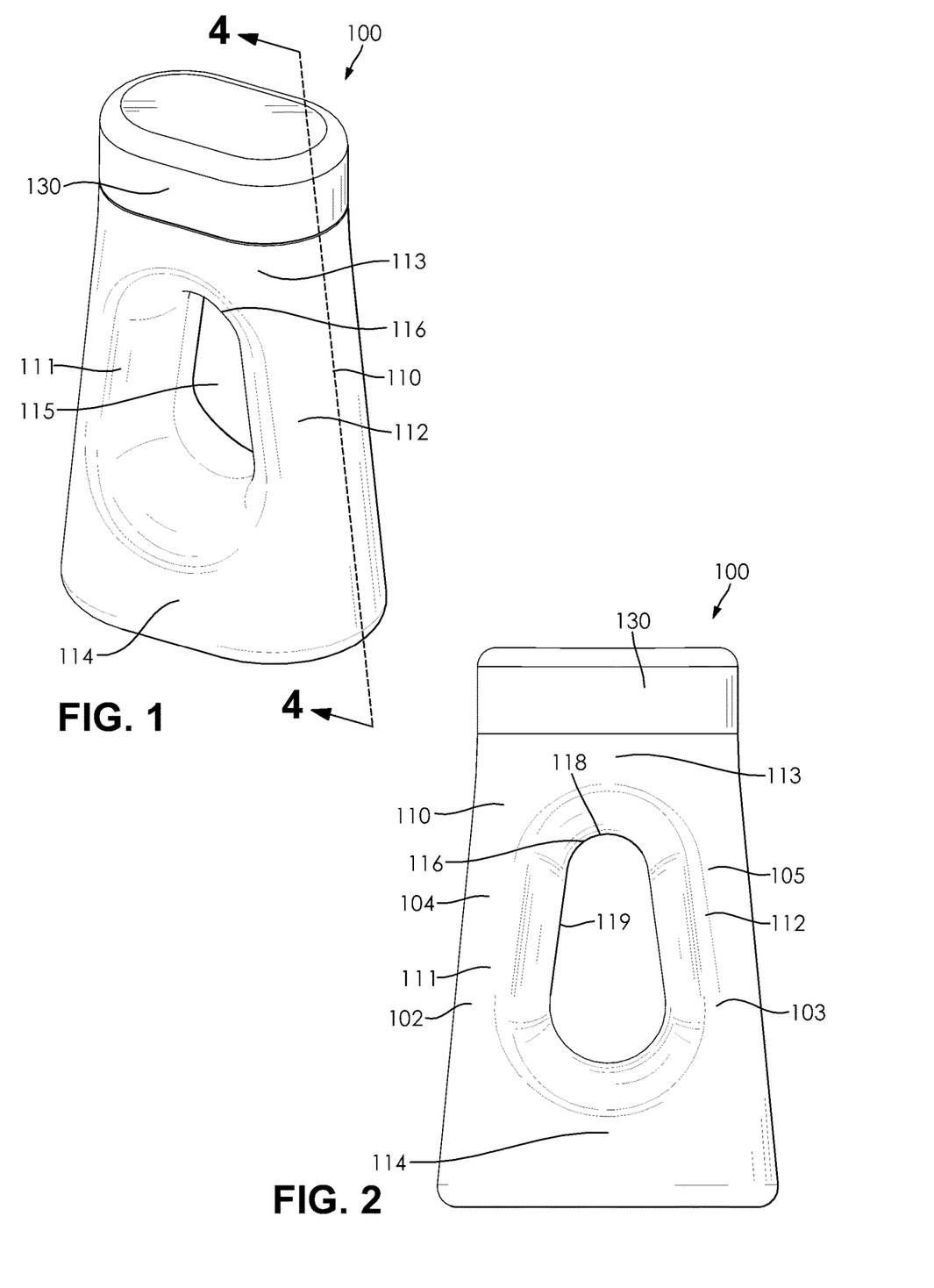
FIG. 1 is a perspective view of a portable urinal in accordance with an embodiment of the present invention.
FIG. 2 is a front view of a portable urinal in accordance with an embodiment of the present invention.
Figure 3:
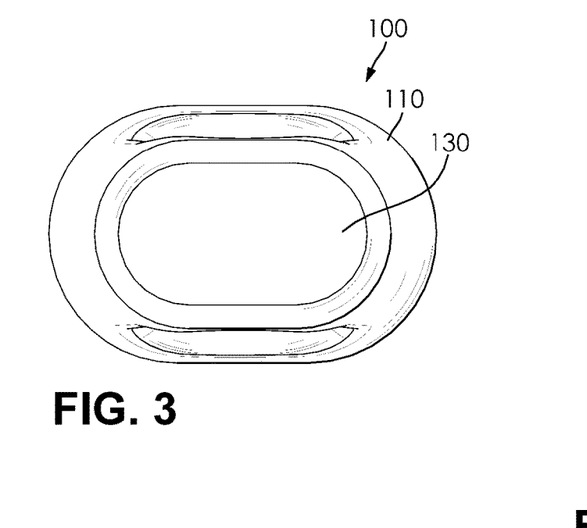
FIG. 3 is a top view of a portable urinal in accordance with an embodiment of the present invention.
Figure 4:
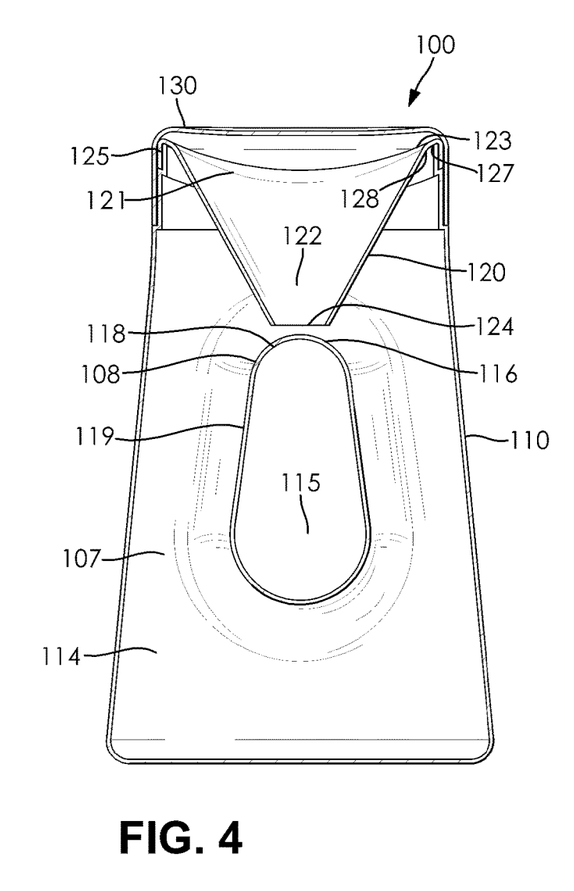
FIG. 4 is a cross-sectional view of a portable urinal in accordance with an embodiment of the present invention taken along the line shown in FIG. 1.
Figure 5:
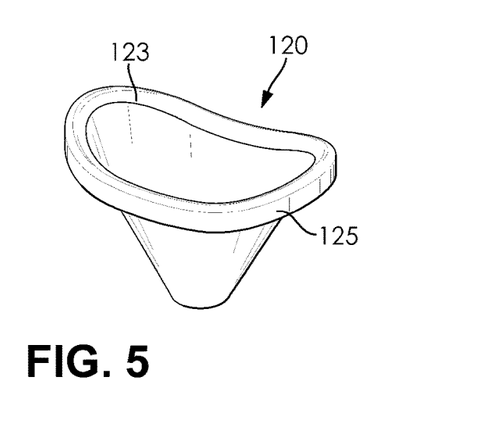
FIG. 5 is a perspective view of a portable urinal funnel in accordance with an embodiment of the present invention.
Figure 6:
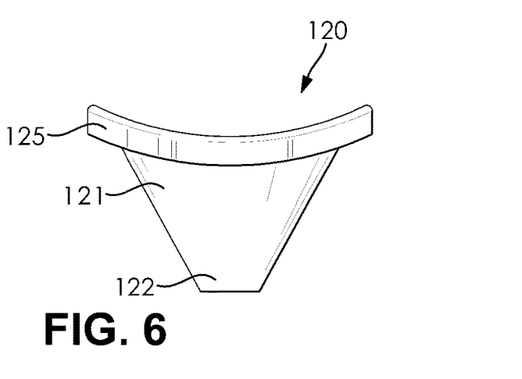
FIG. 6 is a front view of a portable urinal funnel in accordance with an embodiment of the present invention.
Figure 7:
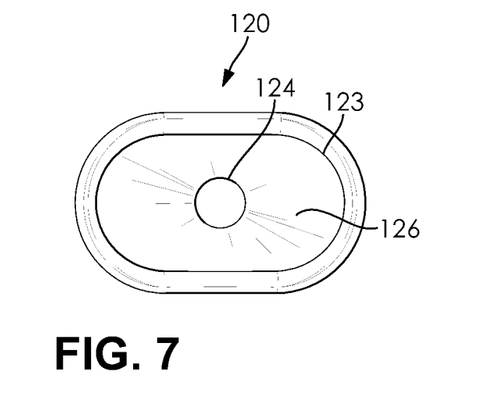
FIG. 7 is a top view of a portable urinal funnel in accordance with an embodiment of the present invention.
Figure 8:
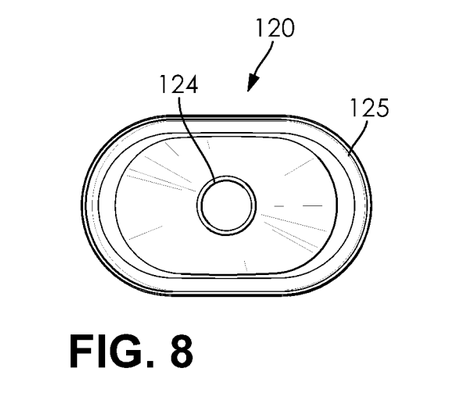
FIG. 8 is a bottom view of a portable urinal funnel in accordance with an embodiment of the present invention.
Figure 9:
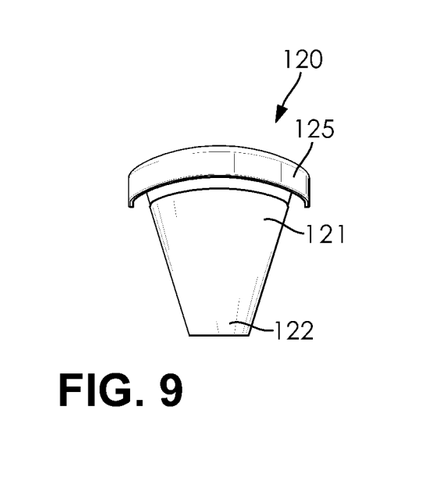
FIG. 9 is a side view of a portable urinal funnel in accordance with an embodiment of the present invention.
Figure 10:
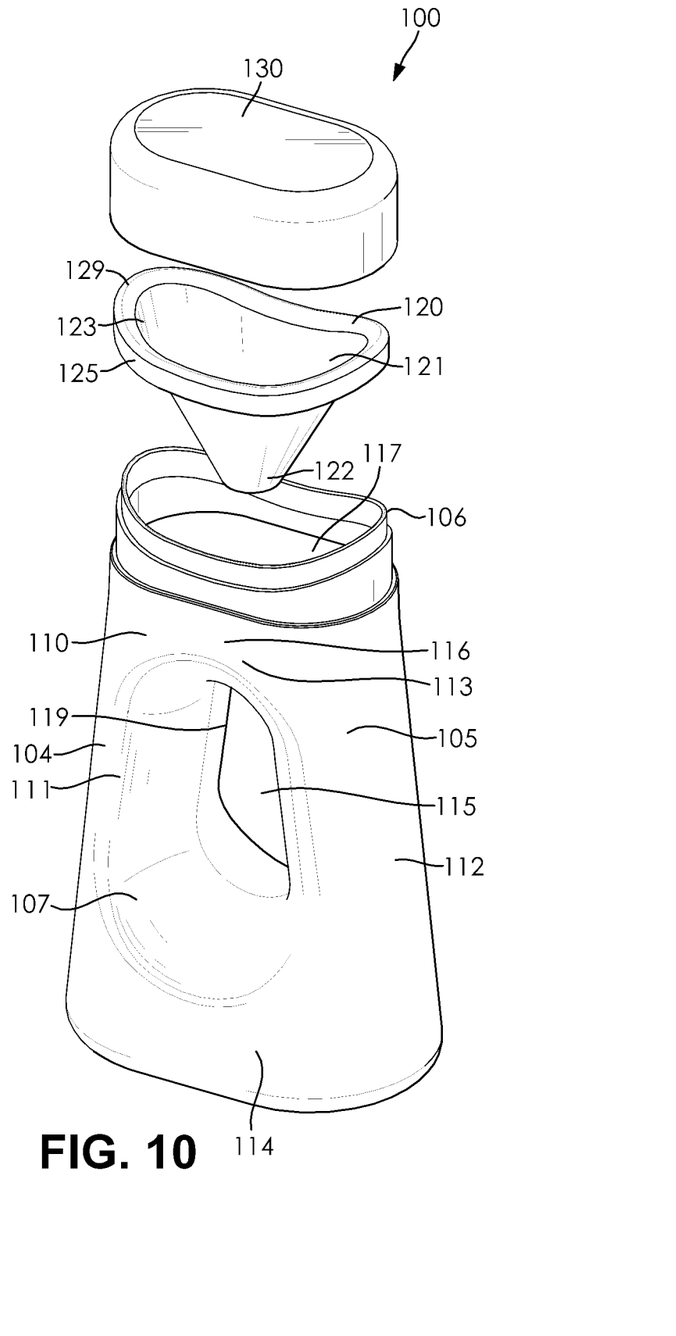
FIG. 10 is a perspective exploded view of a portable urinal in accordance with an embodiment of the present invention.

FIG. 4 depicts a cross-sectional view of an exemplary portable urinal in accordance with embodiments of the present invention. FIGS. 5-9 respectively depict perspective, front, side, top and bottom views of a funnel component in accordance with embodiments of the present invention. FIG. 10 depicts an exploded view of an exemplary portable urinal in accordance with embodiments of the present invention. As demonstrated in FIGS. 4-10, a funnel component 120 may be disposed at a top portion of the body member 110. As shown in the depicted examples, the funnel component 120 may be placed atop an opening 117 in the body member 110. In some embodiments, as in the depicted embodiment, the funnel component 120 may comprise a top section 121 opposing a bottom section 122. The side walls of the funnel component 120 may taper down from the top section 121 to the bottom section 122 to form a conical-shaped funnel.

As shown in the figures, the funnel component may include a first opening 123 at its top section 121 that extends towards a second opening 124 at its bottom section 122. In the depicted example, the first opening 123 is larger than the second opening 124. In some examples, the funnel component 120 may be formed with a lip 125 configured to support connection of the funnel component 120 to the opening 117 of the body member 110. The lip 125 of the funnel component 120 may be configured to snap onto the body member 110. In some scenarios, the lip 125 may correspond to the configuration of the opening 117 of the body member 110. For example, the lip 125 of the funnel component may correspond to indents or protrusions formed on or around the urinal body opening 117. In some examples, the lip 125 may be configured as a border element which may be disposed around the wide top section 121, the lip or border element 125 may have a bottom side 127 formed with a slot 128 adapted to receive an edge portion of the urinal body 100. The funnel component 120 may be detached from the body member 110 for example, to support easy cleaning of the funnel component 120 and/or the body member 110. In some examples, the funnel component 120 may be replaceable, for example, a used funnel component 120 may be replaced with a new funnel component 120.

In accordance with embodiments of the present invention, the urinal 100 may comprise a baffle implement, for example, a fluid deflection wall 118. In some examples, the fluid deflection portion and/or wall 118 may be disposed in a middle section 119 of the urinal 100, for example, the deflection wall 118 may extend from one or more interior side walls of the urinal 100, for example, from a first interior side wall to a second interior side wall of the urinal 100, in a position configured to interrupt the flow of urine entering the urinal 100 through the funnel component 120. In some examples, the deflection wall 118 may be disposed in a position within the urinal 100 substantially opposing (e.g., corresponding to) the position of the bottom end 122 of the funnel component 120. As shown in FIG. 4, in embodiments of the urinal 100 with a hollow recess or void 115 formed in a middle section of the urinal 100, a deflection wall 118 may be formed at a top or apex portion of the side walls defining the hollow recess or void 115. In some embodiments, a middle section 119 of the urinal 100 may be formed with a compression section (e.g., in addition to or in lieu of a hollow recess or void). The compression section may be a section of the urinal 100 where two opposing sidewalls of the urinal 100 meet or connect. In some examples, the compression section may comprise a top portion formed with a deflection wall. In any embodiment, a deflection wall 118 may be formed within the urinal 100, whether or not a void 115 or a compression section is formed in the urinal body 100.

As shown in the figures, in accordance with embodiments of the present invention, a liquid retaining apparatus, for example, a vessel or urinal 100 may comprise two fluid paths 102 and 103, each path 102 and 103 originating at a top end 113 of the vessel being formed with an opening 117 and meeting at a bottom end 114 of the vessel 100 being a reservoir portion, wherein the vessel 100 may further include a middle section 119 comprising a fluid deflection wall 118, and a funnel component 120 having a top section 121 adapted to engage with the top end 113, for example, at the top opening 117, of the vessel 100. In some embodiments, the two fluid paths 102 and 103 of the vessel 100 may be in fluid communication with one another. In some embodiments, a void 115 may be formed through the middle section of the vessel, such that the middle section 119 may define one or more handles, for example, two handles 104 and 105, of the vessel 100. In some embodiments, the funnel component top section 121 may comprise a border element 125 disposed around an edge portion 129 of the top section 121, the border element 125 having a bottom side 127 comprising a slot or groove 128 corresponding to an edge portion 106 of the opening at the top end of the vessel 100 to support secured engagement of the funnel component 120 with the vessel 100. In some examples, the funnel component 120 may be configured to direct liquid towards the deflection wall 118 formed at the middle section of the vessel to dampen sound created by fluids entering the vessel 100. In some scenarios, a cover 130 may be configured to engage with the top end of the vessel 100 and cover the top opening 117 of the vessel 100 and the funnel component 120.

In accordance with embodiments of the present invention, a liquid retaining apparatus in accordance with the present disclosure may be configured as vessel or portable urinal 100 comprising a tubular structure forming a loop 107 having a flat bottom section 114 being a reservoir portion and a top section 113 having an opening 117, wherein the loop 107 may comprise a middle section 119 formed with at least one interior sidewall 108 comprising a top portion with a fluid deflection portion 118, and a funnel component 120 which may have a top opening 123 extending towards a bottom opening 124 and having interior side walls 126 which taper down from the top opening 123 to the bottom opening 124 to form a conical channel. In some embodiments, a lip or lip portion 125 of the funnel component may be disposed around a border of the top opening 123 of the funnel component 120 and may be configured to support connection of the funnel component 120 to an edge portion 106 of the top section 113 of the vessel 100. In some embodiments, a bottom side 127 of the lip portion or border element 125 may be formed with a slot or groove 128 configured to receive a portion of the top section 113, for example, an edge portion 106 of the vessel 100. In some embodiments, the funnel component 120 may be configured to direct liquid towards the deflection wall or portion 118 of the middle section to deflect liquid entering the vessel 100 and limit sound created by fluid entering the vessel 100. In some embodiments, a void 115 may be formed in a middle section 119 of the vessel 100 to form a pair of handles 104 and 105 to enable the vessel 100 to be easily grasped by a user by gripping at least one of the handles 104 or 105 of the pair. In some embodiments, instead, or in addition to the void 115, a compression section may be formed in a middle section 119 of the vessel 100, at a joint or compression point connecting two opposing side walls of the vessel 100 to form a pair of handles 104 and 105 enabling the vessel 100 to be easily grasped by a user by gripping at least one of the handles 104 and 105 of the pair.

In accordance with embodiments of the present invention, a liquid retaining apparatus in accordance with the present disclosure may be configured as vessel or portable urinal 100 comprising a top section 113 with an opening 117 formed with an edge portion 106, a bottom section 114 being a reservoir portion, and two channels 111 and 112 beginning at the opening 117 of the top portion or section 113, diverging at a middle section 119 and meeting at the reservoir or bottom portion 113 of the vessel 100, the two channels 111 and 112 being in fluid communication with one another and each channel 111 and 112 comprising an interior side wall meeting at a middle section 119 of the vessel 100 to form a deflection portion or wall 118, and a funnel member 120 formed as a conical structure tapering from a wide upper or top end 121 to a narrow lower or bottom end 122 and comprising a border element 125 disposed around the wide upper end 121, the border element 125 having a bottom side 127 formed with a slot or groove 128 adapted to receive an edge portion 106 of the vessel, wherein the funnel member 120 may be configured to direct liquid towards the deflection portion 118 of the vessel 100 to dampen sound created by fluids entering the vessel 100. In some embodiments, the funnel member 120 may be formed of a silicon material and the wide upper end 121 of the funnel member 120 may be configured to fit female genitalia to form at least a partial seal, for example, to support use of the vessel 100 as a portable urinal by female users. In some embodiments, the deflection portion 118 may be configured as a baffle to interrupt liquid flow. In some embodiments, the funnel component 120 and deflection portion 118 of the vessel 100 may collectively prevent liquid entering the vessel 100 from making direct contact with the reservoir portion 114 of the vessel. In some embodiments, the edge portion 106 of the vessel may be formed with a depression extending around a perimeter of the top portion 113, the depression corresponding to and adapted to assist the top portion 114 of the vessel 100 to engage with the slot or groove 128 formed in the border element 125 of the funnel member 120. In some embodiments, the middle section 119 may define a void 115 or a compression section (not shown) which may form a pair of handles 104 and 105 configured to enable the vessel 100 to be easily grasped by a user by gripping at least one of the handles 104 or 105.

In accordance with embodiments of the present invention, the portable urinal 100 may be configured with fluid baffling and/or sound dampening features. In some examples, a funnel component 120 and/or a deflection wall 118 may support the sound-dampening functions of the portable urinal 100. For example, the funnel component 120 and/or the deflection wall 118 may be formed of a first layer comprising a thick-walled soft or semi-rigid plastic material, for example, a silicon material having sound-dampening characteristics to dampen the sound of the contact between a stream of urine and the funnel component 120 and/or the deflection wall 118. In some embodiments, the funnel component 120 and/or the deflection wall 118 may include a second layer formed of a sound-dampening material, for example, double-shot silicone. In embodiments of the portable urinal 100 with a void formed in a middle section of the urinal body 100, a top portion of the side walls defining the hollow recess or void 115 may be formed with sound dampening features.

In accordance with embodiments of the present invention, the funnel component 120 may be configured to channel or otherwise direct a stream of fluid entering the portable urinal 100. The funnel component 120 may reduce the flow rate of urine into the urinal 100 and may reduce distance falling urine would otherwise have to travel to arrive at the bottom or reservoir portion of the body member 110, in turn, reducing the sound of the urine introduced into the urinal 100. In some examples, the bottom funnel opening or outlet 124 may be disposed near the apex 116 and/or deflection wall 118 of the body member 110, for example, such that the distance between the opening 124 and the apex 116 and/or the deflection wall 118 is short. In some examples, this short distance may support the sound-dampening feature of the device 100, by decreasing the height (e.g. the distance) falling fluids (e.g. urine) will travel from the funnel 120 to the interior of the body member 110, to minimize or otherwise decrease the sound created by fluids entering the urinal 100. In some examples, the bottom funnel opening 124 may be disposed a distance of 5 millimeters (mm) above the internal apex 116 and/or the deflection wall 118 of the hollow recess 115. In any embodiment, the distance between the bottom funnel opening 125 and the internal apex 116 and/or the deflection wall 118 may be any similarly suitable distance able to minimize the sound created by fluids entering the urinal 100. In some scenarios, the hollow recess 115 of the body member 110 may be configured in a manner that distributes fluids (e.g. urine) into the form of a cascade, for example, over the apex 116 and/or the deflection wall 118 of the body member 110, to diffuse the flow of the fluid over a wide area and dampen the sound of entering fluid.

In accordance with embodiments of the present invention, a portable urinal 100 may be configured to prevent odors from escaping the interior of the portable urinal 100. For example, the funnel component 120 and/or the cover 130 may be configured to substantially close the portable urinal, or otherwise minimize the opening of the portable urinal 100, to retain odors and substantially prevent the odors from escaping the portable urinal 100. In some scenarios, the funnel component 120 may mitigate odor as the funnel component 120 may be designed to prevent the urinal 100 from having an otherwise wide-open mouth or opening.

In accordance with embodiments of the present invention, the portable urinal 100 may be configured to decrease the risk of spills. For example, the funnel component 120 and/or the cover 130 may be configured to substantially cover the opening 117 at the top end 113 of the urinal 100 to decrease the likelihood that contents of the portable urinal 100 will spill if the urinal 100 falls over.

In accordance with embodiments of the present invention, the portable urinal 100 may be configured to be easily cleanable. For example, the funnel component 120 may be removable from the body member 110, for example, separable from the opening 117 at the top end 113 of the body member 110, to enable cleaning of the individual components.

In accordance with embodiments of the present invention, the portable urinal device may have a sleek or ergonomic design. In some examples, the portable urinal 100 may be shaped and dimensioned to be easily carried and moved from place to place. For example, the body member 110, including the two tubular channels 111 and 112 and the hollow recess 115 may be configured to permit a user to hold the urinal 100 from at least the front, back, left- or right-sides of the device 100.

In some scenarios, the wide top opening 123 of the funnel component 120 may support the use of the device 100 by certain users, for example, female users, who may make direct contact with the funnel component 120 when making use of the device 100. In some examples, a silicon funnel component 120 may be soft and may not be as cold as the rest of the components of the urinal device 100 to further support use of the urinal device 100 by female users.

In accordance with embodiments of the present invention, the portable urinal 100 may include a lighting module disposed on the bottom end 114 of the body member 110. In some examples, the weight of the urinal device lighting module may anchor the urinal device 100. For example, the weight of the lighting module may prevent the portable urinal 100 from tipping over to prevent spills. In some examples, the urinal device lighting module may be configured to provide light during nighttime usage. In some scenarios, the urinal device lighting module may be configured to assist users in quickly locating the urinal device 100.

In accordance with embodiments of the present invention, a holder may be provided for docking or holding the portable urinal 100. In some embodiments, the holder may be configured as an accessory for the urinal device 100 and may include a lighting module. In some examples, the holder lighting module may be configured to emit light when the urinal device 100 is placed on it. In some examples, the holder lighting module may be configured to provide light during nighttime usage. In some scenarios, the urinal device lighting module may be configured to assist users in quickly locating the urinal device 100. In some examples, the holder may support an upright position of the urinal device 100.

In any embodiment, the urinal body 100 may be a vessel, container, or other similarly configured liquid retaining apparatus.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some examples," "in some scenarios," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

The term "comprises" and grammatical equivalents thereof are used herein to mean that other components, ingredients, steps, among others, are optionally present. For example, an article "comprising" (or "which comprises") components A, B and C can consist of (i.e., contain only) components A, B and C, or can contain not only components A, B, and C but also contain one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A liquid retaining apparatus, comprising:
a vessel with two fluid paths, each path originating at a top end of the vessel being an opening and meeting at a bottom end of the vessel being a reservoir portion, the vessel including a middle section comprising a fluid deflection wall; and
a funnel component having a top section adapted to engage with the top opening of the vessel, wherein the top section of the funnel component comprises a border element disposed around an edge portion of the top section, the border element having a bottom side comprising a slot corresponding to an edge portion of the opening at the top end of the vessel.

2. The liquid retaining apparatus of claim 1, wherein the two fluid paths are in fluid communication with one another.

3. The liquid retaining apparatus of claim 1, wherein a void is formed through the middle section of the vessel, the middle section defining one or more handles of the vessel.

4. The liquid retaining apparatus of claim 1, wherein the funnel component is configured to direct liquid towards the deflection wall of the vessel to dampen sound created by fluids entering the vessel.

5. The liquid retaining apparatus of claim 1, wherein a cover is configured to engage with the top end of the vessel and cover the top opening of the vessel and the funnel component.

6. A liquid retaining apparatus comprising:
a vessel comprising a tubular structure forming a loop having a flat bottom section being a reservoir portion and a top section having an opening, wherein the loop comprises a middle section formed with at least one interior sidewall comprising a top portion with a deflection portion; and
a funnel component having a top opening extending towards a bottom opening and having interior side walls which taper down from the top opening to the bottom opening to form a conical channel.

7. The liquid retaining apparatus of claim 6, wherein a lip portion of the funnel component is disposed around a border of the top opening of the funnel component and is configured to support connection of the funnel component to an edge portion of the top section of the vessel.

8. The liquid retaining apparatus of claim 7, wherein a bottom side of the lip portion is formed with a slot configured to receive the top section of the vessel.

9. The liquid retaining apparatus of claim 6, wherein the funnel component is configured to direct liquid towards the deflection portion of the middle section to deflect liquid entering the vessel and limit sound created by fluid entering the vessel.

10. The liquid retaining apparatus of claim 6, wherein a void formed in the middle section of the vessel forms a pair of handles enabling the vessel to be easily grasped by a user by gripping at least one of the handles of the pair.

11. The liquid retaining apparatus of claim 6, wherein a compression section formed in the middle section of the vessel forms a pair of handles enabling the vessel to be easily grasped by a user by gripping at least one of the handles of the pair.

12. The liquid retaining apparatus of claim 6, wherein a cover is configured to engage with the top end of the vessel and cover the top opening of the vessel.

13. A liquid retaining apparatus comprising:
- a vessel having a top section having an opening formed with an edge portion, a bottom section being a reservoir portion, and two channels beginning at the opening of the top portion, diverging at a middle section and meeting at the reservoir portion of the vessel, wherein the two channels are in fluid communication with one another and each channel comprises an interior side wall meeting at a middle section of the vessel and forming a deflection portion; and
- a funnel member formed as a conical structure tapering from a wide upper end to a narrow lower end and comprising a border element disposed around the wide upper end, the border element having a bottom side formed with a slot adapted to receive the edge portion of the vessel, wherein the funnel member is configured to direct liquid towards the deflection portion of the vessel to dampen sound created by fluids entering the vessel.

14. The liquid retaining apparatus of claim 13, wherein the funnel member is formed of a silicon material and the wide upper end of the funnel member is configured to fit female genitalia to form at least a partial seal and support use of the vessel as a portable urinal by female users.

15. The liquid retaining apparatus of claim 13, wherein the deflection portion is configured as a baffle to interrupt liquid flow.

16. The liquid retaining apparatus of claim 13, wherein the funnel member and deflection portion of the vessel collectively prevent liquid entering the vessel from making direct contact with the reservoir portion of the vessel.

17. The liquid retaining apparatus of claim 13, wherein the edge portion of the vessel is formed with a depression extending around a perimeter of the top portion, the depression corresponding to and adapted to engaged with the slot formed in the border element of the funnel member.

18. The liquid retaining apparatus of claim 13, wherein the middle section defines a void which forms a pair of handles configured to enable the vessel to be easily grasped by a user by gripping at least one of the handles.

19. The liquid retaining apparatus of claim 13, wherein the middle section defines a compression which forms a pair of handles configured to enable the vessel to be easily grasped by a user by gripping at least one of the handles.

* * * * *